United States Patent
Fan et al.

(10) Patent No.: US 9,581,592 B2
(45) Date of Patent: Feb. 28, 2017

(54) SERS, FLUORESCENCE, ABSORPTION, AND LUMINESCENCE DETECTION WITH FLOW-THROUGH MULTI-HOLE CAPILLARIES

(71) Applicant: THE REGENTS OF THE UNIVERSITY OF MICHIGAN, Ann Arbor, MI (US)

(72) Inventors: Xudong Fan, Saline, MI (US); Yunbo Guo, Ann Arbor, MI (US); Maung Kyaw Khaing Oo, Ann Arbor, MI (US)

(73) Assignee: The Regents Of The University Of Michigan, Ann Arbor, MI (US)

(*) Notice: Subject to any disclaimer, the term of this patent is extended or adjusted under 35 U.S.C. 154(b) by 39 days.

(21) Appl. No.: 14/357,151

(22) PCT Filed: Nov. 8, 2012

(86) PCT No.: PCT/US2012/064200
§ 371 (c)(1),
(2) Date: May 8, 2014

(87) PCT Pub. No.: WO2013/070948
PCT Pub. Date: May 16, 2013

(65) Prior Publication Data
US 2014/0322729 A1    Oct. 30, 2014

Related U.S. Application Data

(60) Provisional application No. 61/557,588, filed on Nov. 9, 2011.

(51) Int. Cl.
*G01N 33/543* (2006.01)
*G01N 21/31* (2006.01)
(Continued)

(52) U.S. Cl.
CPC ....... *G01N 33/54373* (2013.01); *G01N 21/31* (2013.01); *G01N 21/64* (2013.01);
(Continued)

(58) Field of Classification Search
None
See application file for complete search history.

(56) References Cited

U.S. PATENT DOCUMENTS

| 2002/0015149 A1* | 2/2002 | Rahbar-Dehghan .. B01L 3/5025 356/244 |
| 2007/0240773 A1 | 10/2007 | Zimmermann et al. |
| 2010/0210029 A1* | 8/2010 | Meinhart ............... G01N 21/05 436/168 |

OTHER PUBLICATIONS

Fan et al., 'Optofluidic microsystems for chemical and biological analysis', Nature Photonics, Sep. 18, 2011, vol. 5 Issue 10, pp. 591-597.
(Continued)

*Primary Examiner* — Rebecca Martinez
(74) *Attorney, Agent, or Firm* — Harness, Dickey & Pierce, PLC

(57) ABSTRACT

3-dimensional surface-enhanced Raman scattering (SERS), as well as absorption/fluorescence/luminescence detection is carried out using a platform based on nanoparticle-functionalized flow-through multi-hole capillaries for rapid analyte detection. The configuration provides an increased active area and fluidic channels for efficient sample delivery, and also confines and transmits light for a large signal accumulation. Using a capillary consisting of thousands of micron-sized holes adsorbed with gold nanoparticles, a detection limit better than 100 fM is achieved.

15 Claims, 18 Drawing Sheets

(51) Int. Cl.
   *G01N 21/64* (2006.01)
   *G01N 21/65* (2006.01)
   *G01N 21/03* (2006.01)
(52) U.S. Cl.
   CPC ........... *G01N 21/65* (2013.01); *G01N 21/658* (2013.01); *G01N 2021/0346* (2013.01)

(56) References Cited

OTHER PUBLICATIONS

Guo et al., 'Optofluidic Fabry-Perot cavity biosensor with integrated flo-through micro-/nanochannels', Applied Physics Letters, Jan. 24, 2011, vol. 98, Issue 4, pp. 041104-1-041104-3.
Schuster et al., 'Microstructured fibers with highly nonlinear materials', Optical and Quantum Electronics, Dec. 12, 2007, vol. 39, Issue 12-13, pp. 1057-1069.
Buczynski et al., 'Ultra flat supercontinuum generation in silicate dual core microstructured fiber', Laser Physics Letters, Mar. 24, 2009, vol. 6, Issue 8, pp. 575-581.
International Search Report and Written Opinion of the ISA, ISA/KR, mailed Mar. 19, 2013.

* cited by examiner

US 9,581,592 B2

SERS, FLUORESCENCE, ABSORPTION, AND LUMINESCENCE DETECTION WITH FLOW-THROUGH MULTI-HOLE CAPILLARIES

CROSS REFERENCE TO RELATED APPLICATIONS

This application is a 371 U.S. National Phase application of PCT/US2012/064200, filed on Nov. 8, 2012 and published in English as WO 2013/070948 A1 on May 16, 2013, which claims the benefit under 35 U.S.C. §119(e) of U.S. Provisional Patent Application No. 61/557,588, filed Nov. 9, 2011. The entire disclosures of both applications are incorporated herein by reference.

INTRODUCTION

Since its discovery in the 1970s,[1,2] surface-enhanced Raman scattering (SERS) has shown tremendous potential for bio/chemical molecular analysis at the trace and even single molecule level.[3-6] Traditionally, SERS detection is performed on single planar SERS-active surfaces, which are prepared by fabricating nanostructures (nanodomes[7], nano-antenna[8], metal-capped nanopillars[9], nanoporous silicon,[10] and gold[11,12], etc.) on planar substrates (such as silicon wafers) using nanoparticle self-assembly, lithography, nanoimprint, etching, or annealing. However, due to the 2-dimensional (2-D) configurations, the available density of SERS-active sites within the detection volume is limited. Additionally, the 2-D SERS substrates rely on the analytes in bulk solution to diffuse slowly to the SERS-active sites. Therefore, the corresponding SERS detection is time consuming and unfavorable for fast, online, real-time analysis with low sample consumption.

Optofluidics is an emerging field that synergistically integrates optics and microfluidics to significantly enhance the performance of various existing detection techniques, including SERS.[13-18] In the past few years, a number of optofluidic SERS platforms have been investigated.[17,18] For example, photonic crystal fibers (PCFs),[19-23] consisting of a central hollow or solid core surrounded by many air holes, offer inherent fluidic channels for convenient flow-through analyte delivery. In addition, the excitation light and Raman-scattered photons can propagate along the entire length of the PCF, enabling 3-D SERS detection with much larger detection area (and hence higher sensitivity) than the 2-D planar SERS substrate. A detection of 100 pM for rhodamine 6G (R6G) was reported by using either the hollow central core or holey cladding of a PCF as the microfluidic channel and the adsorbed silver/gold nanoparticles as the SERS-active sites.[21,22] An on-chip optofluidic SERS system was also implemented using an antiresonant reflecting optical waveguide (ARROW) structure, which demonstrated a detection sensitivity to a minimum concentration of 30 nM of R6G molecules adsorbed to silver nanoparticles.[24] Porous aluminum membranes,[25,26] benefiting from both large SERS-active surface of thousands of nanochannels within the detection volume and waveguiding capability along the 60 μm long nanochannels, have achieved pico- or zeptogram-level detection of explosives. In addition, step microfluidic-nanochannel junctions were utilized to concentrate analytes or analyte-nanoparticle aggregates near the inlet of the narrower nanochannels, and achieved a detection limit ranging from 3 fM for Cu/Zn-superoxide dismutase aggregates[27] to 10 pM for adenine molecules.[28] Nanoporous materials have also been explored to develop 3-D optofluidic SERS devices. Liu et al. adopted a nanoporous polymer monolith within a microfluidic channel to trap and concentrate silver nanoclusters in a 3-D matrix, which greatly enhanced the SERS intensity and achieve a detection limit of 220 fM for R6G.[29] While significant progress has been made in 3-D optofluidic SERS systems, they still experience either relatively low limited sensitivity,[21,22,24,28] complicated and costly device fabrication procedures,[22,24,27,28] short interaction length unfavorable for large signal accumulation or in-line analyte monitoring,[25,26,29] difficulties in controlling metallic nanoparticle aggregations and nanoclusters,[28,29] or time consuming SERS substrate (i.e., metallic nanoparticle) deposition and analyte accumulation processes.[22,27] How to achieve a simple, reliable, highly sensitive, and cost-effective optofluidic SERS platform still remains unanswered.

SUMMARY

To address these concerns, a method of carrying out a surface analysis of an analyte has been developed. In the method, the analyte is bound to the interior surface of a micro-/nanofluidic channel in a multi-hole capillary. Nanoparticles are immobilized onto the surface with polyelectrolyte mediation; a solution of the analyte is flowed through the capillary to bind the analyte to the nanoparticles. Then the surface bound analyte is excited with electromagnetic radiation or caused to fluoresce or luminesce, and the resulting Raman scattering, fluorescence, absorption, or luminescence of the analyte is detected. Advantageously, the multi-hole capillary provides a plurality of micro-/nanofluidic channels for flow-through analyte delivery, wherein the micro-/nanofluidic channels are characterized by a dimension of 10 nm-200 microns, and wherein the multi-hole capillary does not have photonic confinement.

DESCRIPTION

Figure 1:
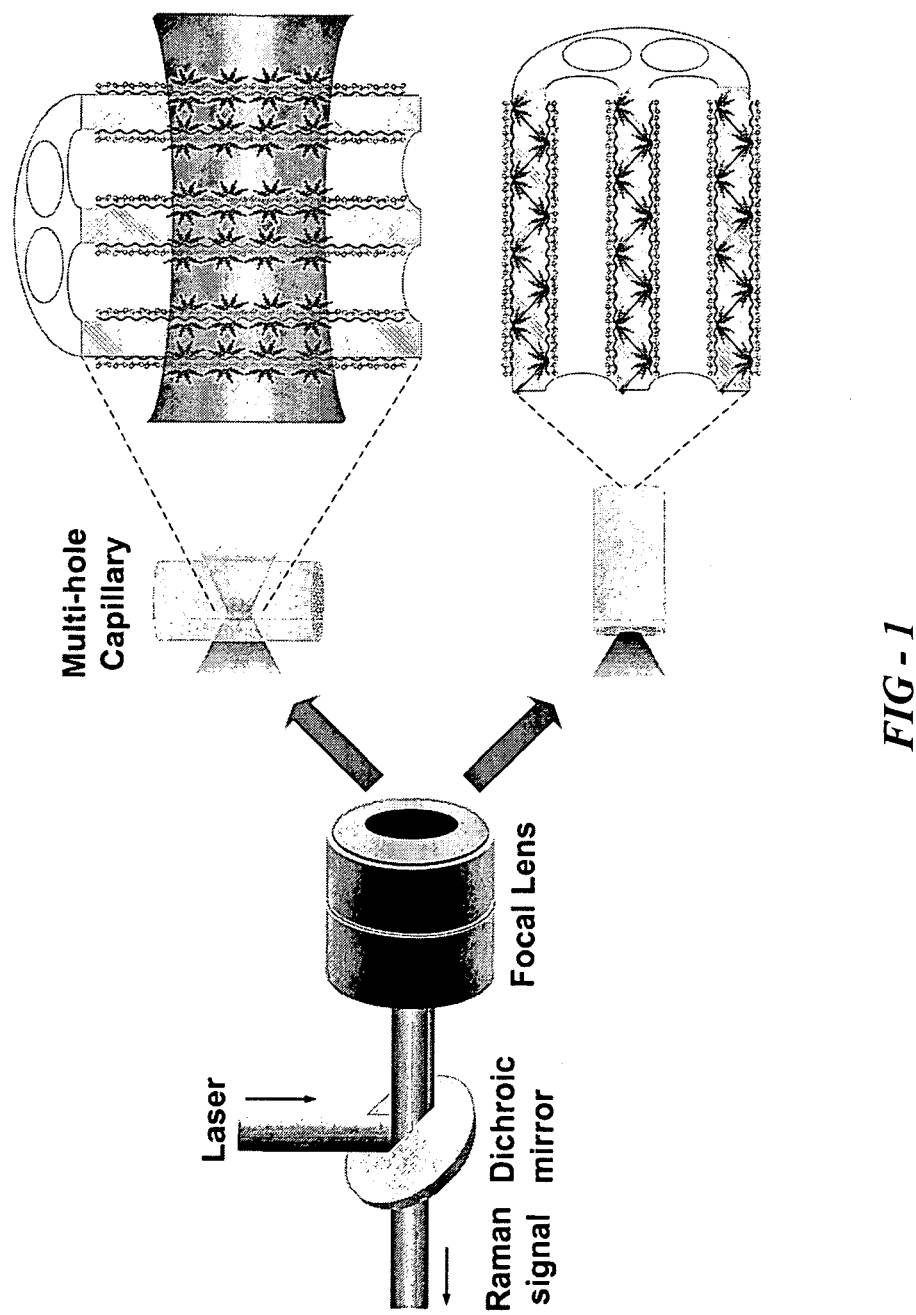
FIG. 1 gives a schematic of a flow-through optofluidic Raman system based on a multi-hole capillary. The SERS excitation and detection are arranged transversely (top) or longitudinally (bottom) with respect to the capillary.

To address the above challenges, here we developed a flow-through 3-D optofluidic SERS platform based on micro-/nanostructured capillaries but avoiding the drawbacks of PCF's and other platforms. An exemplary structure is shown in FIG. 1. Nanoparticles, for example metallic nanoparticles, can be pre-deposited on the inner surface of each micro-/nanofluidic channel before an analyte is flowed through. Alternatively or in addition, the nanoparticles can be pre-mixed with the analyte before being injected into the capillary and subsequently deposited on the inner surface of the channels.

Detection can be carried out in two configurations, transverse and longitudinal detections, where excitation and collection are perpendicular to and along the capillary, respectively, as illustrated in FIG. 1. Both of the detection configurations provide unique advantages.

For example, in the transverse method, the SERS signal is from the SERS-active sites within the detection volume determined by the laser excitation and the SERS collection optics. Due to the extremely large surface-to-volume ratio resulting from thousands of micro/nano-sized holes in the capillary, 3-D sensitive SERS detection can be achieved. This sensitivity is not achieved when using PCF's in the transverse detection, because of thick silica cladding. In addition, the flow-through channels enable robust and reliable nanoparticle immobilization, and fast and convenient sample delivery for subsequent in-line SERS detection. Furthermore, the flow-through capillary with micro/nano-sized holes combines convective flow and short diffusion length scales, which significantly reduces the time required for analyte molecules to reach the SERS-active surfaces.[30, 31]

The longitudinal detection method takes additional advantage of SERS signal accumulation along the capillary. The excitation light is guided within the wall (silica) via total internal reflection (especially within the triangular junctions formed by three holes along the capillary[22,32,33]) and quasi-guided by the hole via multi-reflection.[32] The SERS generated by the excitation light is then coupled back to and guided by the wall and hole. As a result, the SERS signal accumulates along the capillary but also experiences progressive loss due to the scattering/absorption of gold nanoparticles. Therefore, the overall backward or forward propagating SERS intensity is expected to be the sum of the SERS signal gain and its scattering/absorption loss over the whole capillary length.[23] Consequently, the well-defined flow-through micro-/nanochannels are able to increase the SERS accumulative length as a PCF does, a distinct advantage over the short-length porous aluminum membrane[25,26] and non-waveguiding porous polymer monolith.[29]

In addition, in contrast to the PCF or other micro structured optical fibers 19,34 where the SERS-active area (or the areas active for luminescence or fluorescence) is limited to the central core or hole as light is tightly confined there by the photonic crystal structure consisting of precisely arranged surrounding holes, the multi-hole capillary described here does not have the photonic crystal structure of the PCF. As a result, each hole (or channel) can work independently as the SERS-active substrate. Therefore, the excitation light can be at any wavelength and can reach all channels within the capillary, which greatly increases the sensing surface area. Moreover, the multi-hole capillary does not need delicate effort to arrange the holes to construct the photonic crystal structure, and therefore, it can be fabricated with the same fiber drawing method as for PCF, but more easily and more cost-effectively.

The 3-D optofluidic SERS platform can be used for absorption, luminescence, and fluorescence detection as well as surface enhanced Raman scattering. In exemplary embodiments, absorption and fluorescence are used to detect analytes that bind to antibodies on the surface, or that are substrates (either as starting material or as reaction product) of enzymes that are part of an antibody-containing bound complex, as in otherwise conventional ELISA applications.

The so-called multi-hole capillaries (also designated as micro- or nanostructured) are characterized by a plurality of flow through micro-/nanofluidic channels with sizes on the order of about 100 nm up to about 200 microns, or from about 1 micron to about 5 microns. The channels provide a large surface area for binding of analytes, leading to enhanced detection.

In one embodiment, a method is provided of detecting an analyte bound to a surface by use of surface enhanced Raman scattering by exciting the analyte with electromagnetic radiation and detecting the Raman scattering. The surface onto which the analyte is bound is the interior surface of a micro-/nanofluidic channel in a multi-hole capillary. The multi-hole capillary provides a plurality of micro-/nanofluidic channels for flow-through analyte delivery, the micro-/nanofluidic channels are characterized by a dimension of 10 nm-200 microns, for example 100 nm-200 microns, and the multi-hole capillary does not have a photonic crystal structure.

In another embodiment, a method of detecting an analyte bound to a surface by use of absorption or fluorescence spectroscopy involves exciting the analyte with electromagnetic radiation and detecting the resulting absorption or fluorescence. As with the SERS application, the surface onto which the analyte is bound is the interior surface of a micro-/nanofluidic channel in a multi-hole capillary, wherein the multi-hole capillary provides a plurality of micro-/nanofluidic channels for flow-through analyte delivery, wherein the micro-/nanofluidic channels are characterized by a dimension of 10 nm-200 microns, for example 100 nm-200 microns, and wherein the multi-hole capillary does not have photonic confinement. In a variation, the methods involve detection of luminescence arising from the bound analyte in the same way.

In yet another embodiment, a method of detecting an analyte by use of absorption or fluorescence spectroscopy involves exciting the analyte with electromagnetic radiation and detecting the absorption or fluorescence, wherein the analyte is bound to the surface as part of an antibody complex or is the substrate of an enzyme attached to an antibody attached to the interior surface of a micro-/nanofluidic channel in a multi-hole capillary, wherein the multi-hole capillary provides a plurality of micro-/nanofluidic channels for flow-through analyte delivery, wherein the micro-/nanofluidic channels are characterized by a dimension of 10 nm-200 microns, for example 100 nm-200 microns, and wherein the multi-hole capillary does not have a photonic crystal structure.

In these and other methods, the multi-hole capillary is made of fused silica glass or borosilicate glass or polymer (e.g. high density polyethylene, polymethylmethacrylate, polytetrafluoroethylene, or polystyrene).

In a related embodiment, a method of carrying out a surface analysis of an analyte bound to the interior surface of a micro-/nanofluidic channel in a multi-hole capillary involves immobilizing nanoparticles onto the surface with polyelectrolyte mediation, flowing a solution of the analyte through the capillary to bind the analyte to the nanoparticles, exciting the surface bound analyte with electromagnetic radiation, and detecting Raman scattering, fluorescence, absorption, or luminescence of the analyte. In common with the other embodiments, the multi-hole capillary provides a plurality of micro-/nanofluidic channels for flow-through analyte delivery, the micro-/nanofluidic channels are characterized by a dimension of 10 nm-200 microns, for example 100 nm-200 microns, and the multi-hole capillary does not have a photonic crystal structure.

In another embodiment, an analysis plate for enhanced detection of analytes by SERS, fluorescence, absorption, or luminescence comprises a solid substrate containing first and second major surfaces and having one or a plurality of through holes connecting the first and second surfaces. At least one through hole, and preferably a plurality or all of them, contain a multi-hole capillary that provides a plurality of micro-/nanofluidic channels for flow-through analyte delivery, wherein the micro-/nanofluidic channels are characterized by a dimension of 10 nm-200 microns, for example 100-200 microns, and wherein the multi-hole capillary does not have a photonic crystal structure.

In all of these embodiments, the multi-hole capillaries are also characterized by the number of micro-/nanofluidic channels contained in the capillary. Useful platforms contain from 10 to 300,000 channels, for example 100-3000,000; 200-300,000; 1000-300,000; 1000-20,000; and 1000-10,000. They are made of glass in a preferred embodiment, for example fused silica glass and borosilicate glass, by way of non-limiting example. The channels can be round or of another shape, with dimensions on the order of a hundred or so nanometers up to 10 or so microns. The dimensions are, in non-limiting embodiments, 10 nm-200 microns, 50 nm-200 microns, 100 nm-200 microns, 100 nm-100 microns, 100 nm-50 microns, 100 nm-20 microns, 200 nm-20 microns, 500 nm-20 microns, 1-20 microns, and 1-5 microns.

The multi-hole capillaries are also characterized by not having a photonic crystal structure. This feature distinguishes them from photonic crystal fibers (PCFs) and permits the use of light of a wide range of wavelengths (including white light) to be used in excitation and detection of the scattering, absorption, or fluorescence being probed by the methods described herein.

In the methods described herein, excitation and detection are carried out either in a longitudinal or a transverse configuration. There are four combinations: transverse excitation and transverse detection; transverse excitation and longitudinal detection; longitudinal excitation and transverse detection; and longitudinal excitation and longitudinal detection.

In exemplary embodiments, we used a multi-hole capillary with 2700 micron-sized flow-through holes and ~120 nm gold nanoparticles as a model system to demonstrate the flow-through 3-D optofluidic SERS platform. The multi-hole capillary is characterized by a structure that does not exhibit photonic confinement but instead transmits light of all the incident frequencies. Both transverse and longitudinal detection were made possible with the system. Ultrasensitive SERS detection of low concentrations of molecules adsorbed on discrete gold nanoparticles was achieved with a detection limit better than 100 fM, a sampling time less than 5 minutes, and a data acquisition time of 2 seconds.

EXAMPLES

Figure 2:
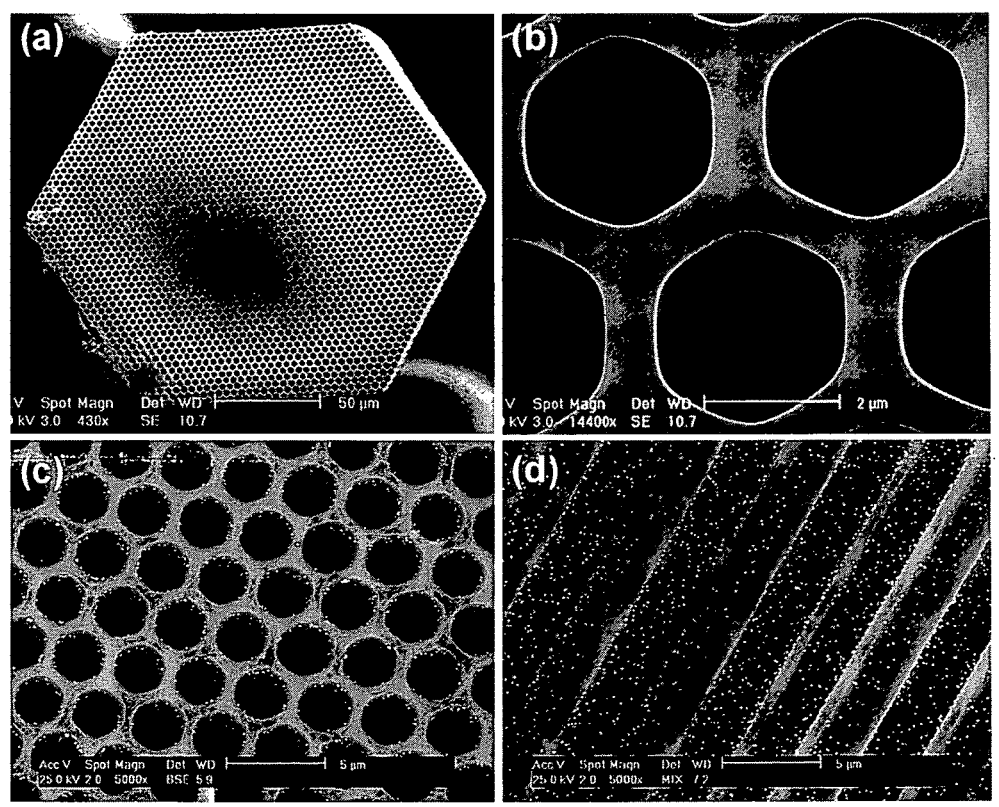
FIG. 2 (a) provides scanning electron microscopy (SEM) images of the multi-hole capillary with the outer diameter of 190 μm, hole size of 2.9 μm, and wall thickness of 0.7 μm. (b) The enlarged images of the holes. (c) The facet of the capillary adsorbed with gold nanoparticles. (d) Cross section of flow channels with adsorbed gold nanoparticles.

The flow-through multi-hole capillaries used in our experiments were 190 μm in outer diameter and had 2700 uniform 2.9-μm holes with 0.7-μm thick wall between two adjacent holes (see FIGS. 2(a) and (b)). They were fabricated using an in-house computer controlled fiber/capillary drawing system and a borosilicate glass preform (1.30 mm outer diameter and 18 μm hexagonal holes).

Transverse Detection

We first investigated the proposed SERS platform using the transverse detection method. All Raman and SERS measurements were carried out with the custom made Raman spectroscopy system with a 785 nm diode laser focused using an aspheric lens (NA=0.55 and f=4.51 mm) to produce a spot size of approximately 3 μm in diameter with 6 mW of optical power. The corresponding detection volume is approximately $1.6 \times 10^3$ μm$^3$ (or 1.6 pL) which is determined by the excitation laser spot size and Raman signal collection optics (120 μm collection depth across the capillary) (see FIG. 12). Due to the nature of 3-D detection, the total surface area within the detection volume is estimated to be $2 \times 10^3$ μm$^2$, over two orders of magnitude larger than 7 μm$^2$ obtained with a single flat surface using the same excitation and collection optics.

Figure 13:
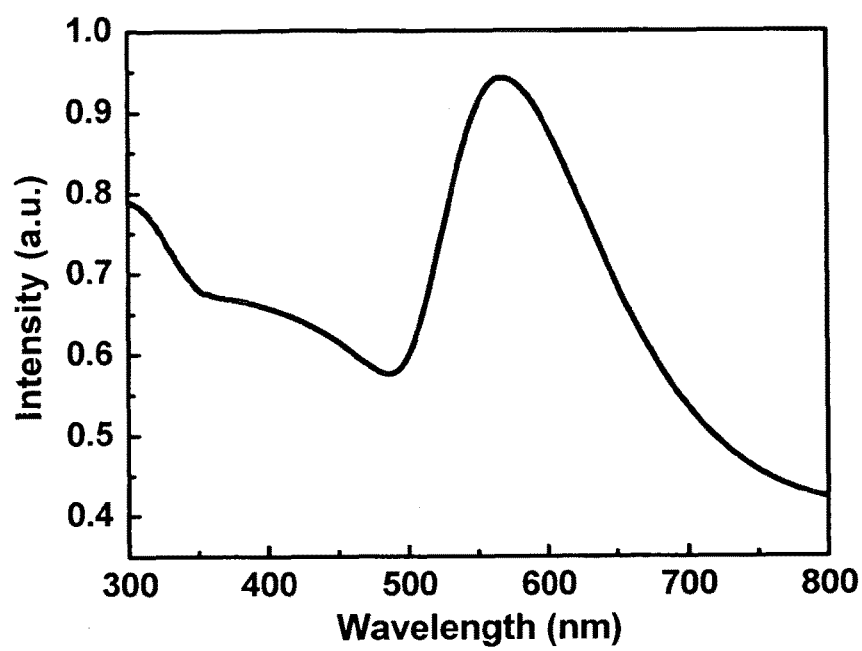
FIG. 13 shows the extinction spectrum of gold nanoparticles measured in solution.

The multi-hole capillary with micron-sized flow channels also enables large sized gold nanoparticles to be immobilized onto the inner surface for high SERS enhancement.[35] In the experiments, we used gold nanoparticles of 117±20 nm in diameter, which were synthesized by the modified UV-assisted photo-chemical method as described previously[35] and had a resonance wavelength of 570 nm (see FIG. 13). Immobilization of gold nanoparticles onto the inner surface (silica) of the capillary was achieved through polyelectrolyte mediation. First, polyallylamine hydrochloride (PAH) was flowed through a long capillary (~20 mm) and allowed to adsorb on the channel surface, providing anchoring sites for gold nanoparticles. Then, a 3 mm long portion of the PAH-treated capillary was cut and mounted on a needle connected to a syringe. Gold nanoparticles or the mixture of gold nanoparticle and analytes were loaded into the capillary through atmospheric pressure. Due to the high capturing efficiency associated with the micro-/nanostructured channel,[30,31] the sample consumption required for SERS detection can be significantly reduced. In our experiments, only 2 μL solution was used to flow through the capillary within 5 minutes. FIGS. 2(c) and (d) show the typical scanning electron microscopy (SEM) images for gold nanoparticles adsorbed in the multi-hole capillary. Inside the flow channels, discrete gold nanoparticles were quite uniformly distributed on the surface area with a density of 6.1±0.5 particles/μm$^2$, except a few sparked dimers or trimers.

The performance of the flow-through multi-hole capillary for Raman spectroscopy was then characterized with the well-studied molecule probe R6G dye. In order to fully attach R6G molecules to gold nanoparticles for enhancement, we mixed the R6G solution and gold nanoparticles solution with a predetermined ratio for several minutes before loading the mixture into the capillary, similar to others' work reported earlier.[4,6] This procedure made it easier for us to estimate the number of R6G molecules detected by using the number of gold nanoparticles within the laser probe area, under the assumption that R6G molecule and gold nanoparticle were stoichiometrically bound to each other.

Figure 3:
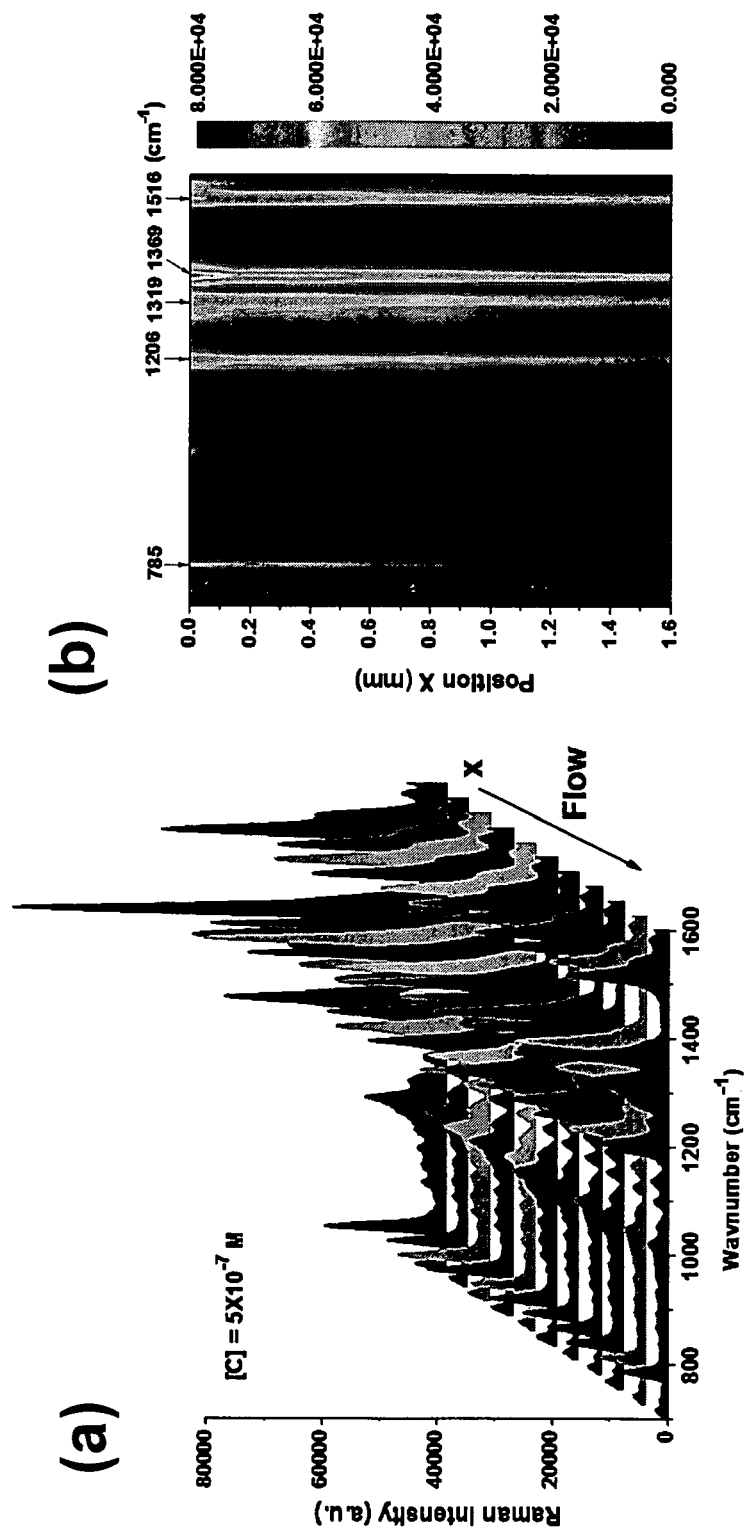
FIG. 3(a) shows a series of SERS spectra for $5 \times 10^{-7}$ M R6G obtained by the stepwise measurement along the capillary in an increment of 160 μm. All spectra were acquired using the transverse detection method with 6 mW of excitation power and 2 seconds of integration time, no post data processing except 5-point adjacent-averaging smooth.
FIG. 3(b) shows a SERS intensity distribution along the capillary extracted from 3(a).

Typical SERS spectra for R6G at the concentration of $5 \times 10^{-7}$ M were taken stepwise at a 160 μm interval from the capillary head to a position 1.6 mm downstream, as plotted in FIG. 3(a). Distinctive Raman shifts at 785, 1206, 1319, 1369, and 1516 cm$^{-1}$ can be observed, which are associated with characteristic vibration modes of C—H band and aromatic C—C stretching band of R6G, respectively.[36] Since nanoparticle transport is dominated by convection in the microfluidic channel,[37] the gold nanoparticle density adsorbed onto the PAH-modified channel surface gradually decreases along the flowing direction, as reflected by the gradually reduced SERS signal in FIGS. 3(a) and (b). Note the decrease in the SERS intensity is monotonic without any abrupt change, suggesting that the SERS signal results mainly from discrete single nanoparticles rather than nanoclusters or aggregations, which would cause large fluctuations in the SERS intensity distribution along the capillary. All the results indicate that the gold nanoparticle functionalized multi-hole capillary has achieved large SERS-active surface area and reliable SERS-active sites for subsequent SERS detection.

To investigate the capability of the flow-through optofluidic SERS platform, we tested a series of low concentrations of R6G solutions from $5 \times 10^{-10}$ M to $5 \times 10^{-13}$ M, which were prepared by mixing the R6G solutions of $1 \times 10^{-9}$ M to $1 \times 10^{-12}$ M with $4 \times 10^{11}$ particles/mL gold nanoparticle at a 1:1 ratio in volume, respectively. Assuming that all the R6G molecules are attached to the gold nanoparticles, the ratio between R6G molecules and gold nanoparticles is 1:1, 1:10, 1:100, 1:1000 for the R6G concentration of $5 \times 10^{-10}$ M, $5 \times 10^{-11}$ M, $5 \times 10^{-12}$ M, $5 \times 10^{-13}$ M, respectively. Note that each nanoparticle is expected to contain mostly zero or one R6G molecule according to the Poisson distribution for those low R6G concentrations. Based on the gold nanoparticle density of 6.1 particles/μm$^2$ obtained previously, we estimate that $1.2 \times 10^4$ gold nanoparticles are within the detection volume, corresponding to $1.2 \times 10^4$, $1.2 \times 10^3$, $1.2 \times 10^2$ and 12 R6G molecules, respectively, for the R6G concentrations mentioned above, which results in a much larger SERS signal than in the 2-D planar SERS detection.

Figure 4:
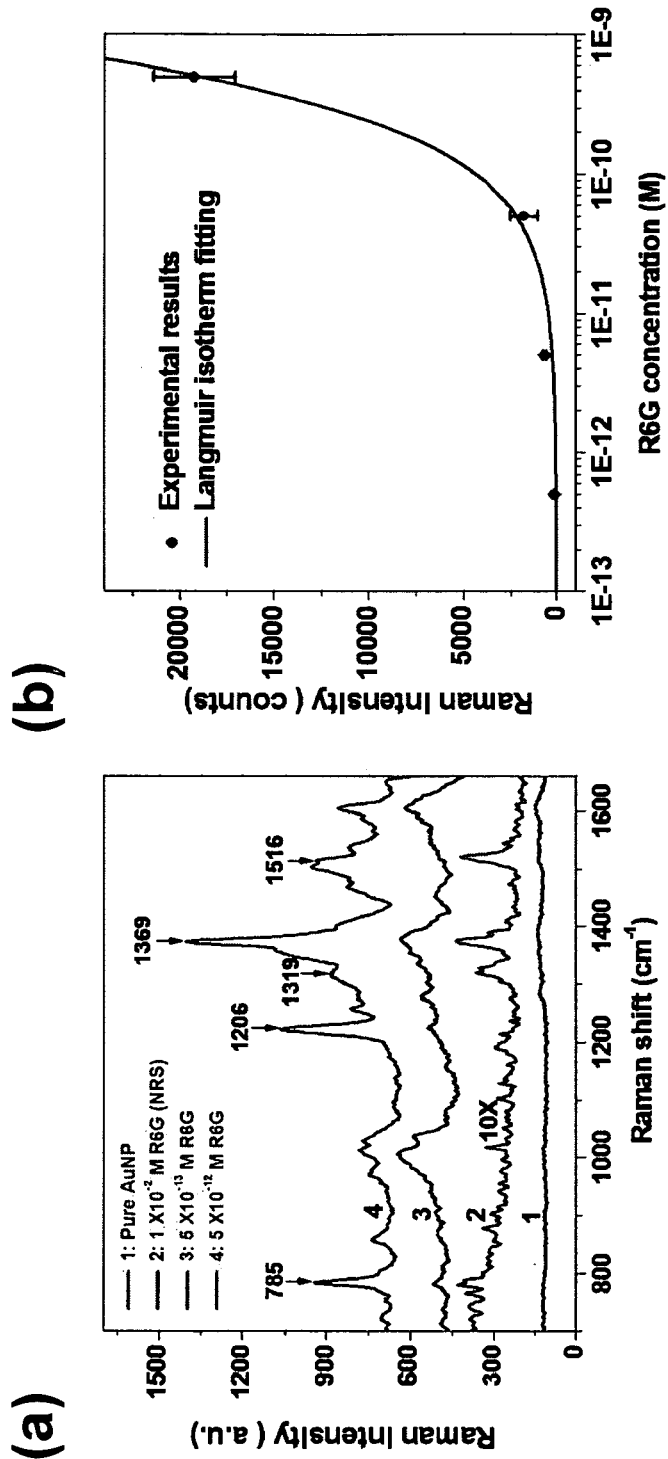
FIG. 4(a) shows SERS spectra of different concentrations of R6G (0, $5 \times 10^{-13}$ M, $5 \times 10^{-12}$ M) using SERS-active capillary, and normal Raman spectrum (NRS) of $1 \times 10^{-12}$ M R6G in solution in a glass cuvette (size: 10 mm×10 mm×10 mm) (with 10 times magnification).
FIG. 4(b) shows SERS intensity at 1369 cm$^{-1}$ for a series of concentrations of R6G from $5 \times 10^{-13}$ M to $5 \times 10^{-10}$ M. Error bars were obtained with at least 3 runs. The solid curve shows the Langmuir isotherm fit to the experimental data.

FIG. 4(a) shows the SERS spectra of R6G at concentration of $5 \times 10^{-12}$ M and $5 \times 10^{-13}$ M. For comparison, the SERS spectrum of pure gold nanoparticles in the absence of R6G and the normal Raman spectrum (NRS) of R6G at the concentration $1 \times 10^{-2}$ M in a 1-mL glass cuvette are also shown. The characteristic R6G peaks are clearly observed for $5 \times 10^{-12}$ M, despite some differences from the normal Raman spectrum, which are expected as the interaction between the molecules and gold nanoparticles results in conformation changes and variations in molecular vibration modes. For R6G with the concentration of $5 \times 10^{-13}$ M, although fewer than 12 R6G molecules are within the detection volume, according to the above calculation, the SERS peaks at 785 cm$^{-1}$ and 1369 cm$^{-1}$ are still observable to indicate the presence of R6G molecules, attesting to the excellent sensing performance of the multi-hole capillary as the optofluidic SERS platform.

The enhancement factor (EF) of the proposed SERS system can be estimated using the following equation:[38]

$$EF = (I_{SERS}/I_{norm})(N_{norm}/N_{SERS}),$$

where $I_{SERS}$ and $I_{norm}$ are the measured Raman intensity or SERS and NRS, respectively. $N_{norm}$ and $N_{SERS}$ are the number of R6G molecules in the detection volume for NRS and SERS, respectively. We used the strongest signature stretching mode at 1369 cm$^{-1}$ at $5 \times 10^{-12}$ M for SERS and $1 \times 10^{-2}$ M for NRS shown in FIG. 4(a). The number of R6G molecules detected is 120 for $5 \times 10^{-12}$ M solution in SERS and $9.8 \times 10^9$ for $1 \times 10^{-2}$ M solution in NRS. With 35× higher Raman intensity for SERS, the EF is calculated to be $2.9 \times 10^9$. Referring to our previous results,[35] we estimate that $10^6$-$10^7$ fold enhancement results from the gold nanoparticle adsorbed on the capillary surface. Additional $10^2$-$10^3$ fold enhancement may be attributable to the light confinement and multiple surface reflections or scattering of the multi-hole capillary. To verify this, a control experiment was performed to measure the normal Raman spectra of $1 \times 10^{-2}$ M R6G in the multi-hole capillary and showed over 20 fold enhancement in NRS (and hence the light intensity inside the capillary) could be achieved as compared to the same experiment performed using a 1-mL glass cuvette (see FIG.

14). In the presence of gold nanoparticles, we speculate that a higher enhancement may be obtained due to multiple photon scattering.

The limit of detection (LOD) for the multi-hole capillary optofluidic SERS system was also evaluated by varying R6G concentrations, then measuring the intensity of characteristic R6G band at 1369 cm$^{-1}$ at a position with maximum signal along the capillary (mostly close to the liquid inlet), as plotted in FIG. 4(b). The experimental data could be well fit by a Langmuir isotherm curve with nonlinear least-squares regression.[36] By substituting 3 standard deviations of the blank signal into the fitted Langmuir isotherm curve, an estimated LOD of 70 fM is obtained, which is three orders of magnitude better than that achieved with a long PCF with discrete gold nanoparticles,[21,22] and similar to that in the polymer monolith with silver nanoparticle aggregations.[29]

Longitudinal Detection

Figure 5:
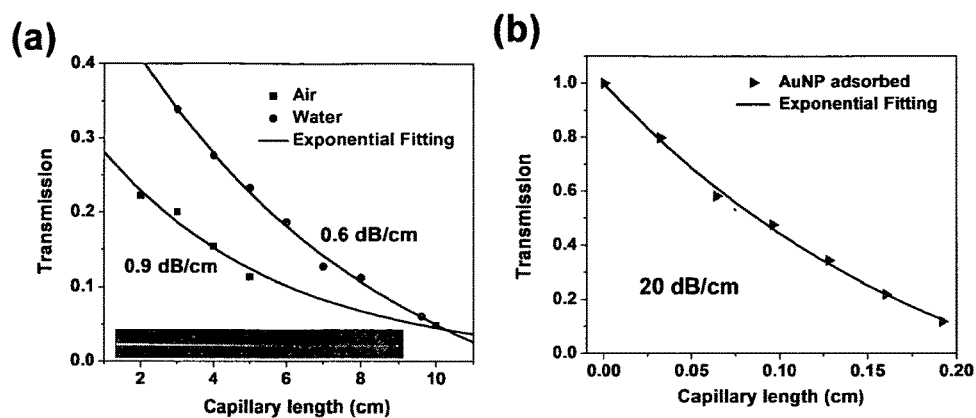
FIG. 5(a) shows transmission loss for multi-hole capillary filled with air or water. The inset shows the picture of light propagating within the capillary.
FIG. 5(b) shows transmission loss for gold nanoparticle-functionalized capillary.

Apart from excellent performance achieved with the transverse direction, further improvement is possible with the longitudinal measurement by accumulating SERS intensity along the capillary. We first investigated the light guiding properties of the multi-hole capillary. As shown in the inset of FIG. 5(a), the light propagation can be observed along the capillary for a long distance of 10 cm. Using the cut-back method with the same optical system, we measured the transmission loss to be 0.9 dB/cm and 0.6 dB/cm for air and water filled capillary, respectively. Clearly, when the gold nanoparticles adsorbed onto the inner surface of the capillary, transmission loss is expected to be much larger due to the nature of absorption and scattering of the metallic nanoparticles. However, it is difficult to measure the transmission loss of a much shorter (~3 mm) capillary immobilized with gold nanoparticles using the cut-back method experimentally, we quantified the scattered light from the same excitation source (785 nm diode laser) at different locations of the capillary along the light propagation direction (see FIG. 15). As expected, the transmission loss dramatically increased to 20 dB/cm (see FIG. 5(b)), similar to what was reported earlier.[34] Such a large transmission loss indicates that the multi-hole capillary allows large field-metal nanoparticle interaction for SERS enhancement.[22,34] The characteristic length for 3 dB loss is 1.50 mm, which implies that the proposed optofluidic SERS system is able to excite and collect the SERS with an effective length of 0.75 mm along the capillary, quite consistent with the results obtained in FIG. 3.

Figure 6:
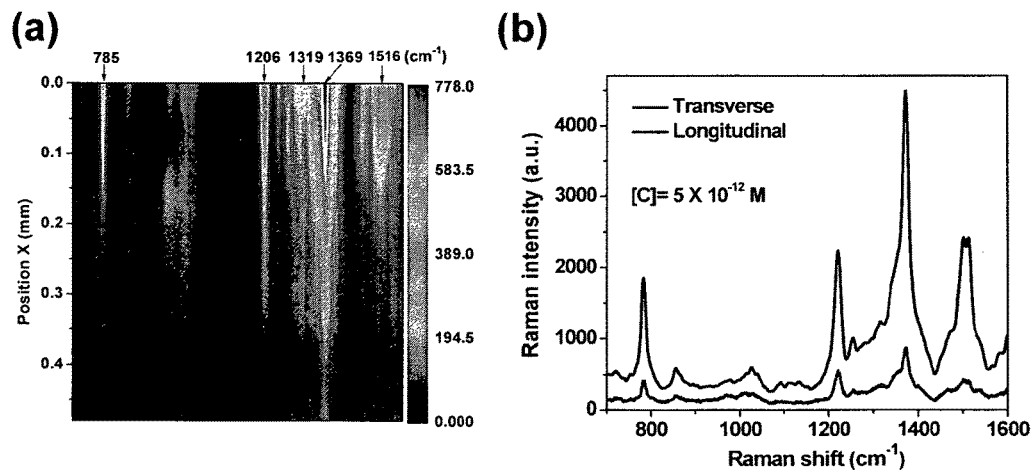
FIG. 6(a) shows SERS intensity distribution along the capillary in the transverse direction.
FIG. 6(b) gives a comparison of SERS intensity in the transverse and longitudinal detection using the same multi-hole capillary adsorbed with the mixture of R6G molecules and gold nanoparticles.

To demonstrate the advantage of using the longitudinal detection, we used the multi-hole capillary with a 2 µL mixture with the final concentration of 5×10$^{-12}$ M R6G and 2×10$^{11}$ particles/mL gold nanoparticle. We first measured the SERS intensity at several positions along the capillary using the transverse detection and found continuous SERS signal along the capillary (FIG. 6(a)). Then we switched to measure the SERS intensity along the longitudinal direction. Even without optimization of the capillary (such as endface flatness) for better SERS collection efficiency, more than 5.5 times higher SERS signal is achieved than the maximum signal in the transverse direction (FIG. 6(b)), which suggests that the capillary has the ability to accumulate SERS signal. The total EF in the longitudinal direction is estimated to be over 10$^{10}$, and the LOD is estimated to be 14 fM.

Materials

Gold (III) chloride solution (30 wt. % of HAuCl$_4$ in dilute HCl), Poly(allylamine hydrochloride) (PAH) (average molecular weight of 15,000 g/mol), sulfuric acid (96.0%, Acros Organics, ACS reagent), were purchased from Sigma-Aldrich, USA. Sodium citrate (enzyme grade) was purchased from Fisher Scientific, USA. They were used without further purification. Milli-Q water was filtered by Quantum Ex, Ultrapure Oranex Cartridge (Millipore) filtration columns and used for all experiments. All glassware were cleaned overnight in the mixture solution prepared by dissolving 120 g of Nochromix® (Godax Laboratories, Inc., MD, USA) powder in 3.78 liters of concentrated sulfuric acid and were then thoroughly rinsed with Milli-Q water.

Fabrication and Treatment of a Multi-Hole Capillary

The microstructured multi-hole capillary was fabricated using an in-house computer controlled fiber/capillary drawing system and a borosilicate glass preform obtained from Incom. Inc, Charlton, Mass. Specially, the multi-hole capillary has 2700 uniform hexagonal holes with 20-µm size. Before pulling, the perform was illuminated under UV light for 1 hour, then put in ethanol cleaning in ultrasound for 30 minutes, and illuminated under UV light for another 1 hour. To keep a certain air pressure inside the channels, a piece of 5 cm long preform was used and sealed both ends using glue. Suitable heating time, feeding and pulling speeds are chosen to pull a long capillary. The pulled capillary is treated with the same way before use. After treatment, a desirable length of capillary (such as 3 mm) was assembled into a flat-end needle. 0.05 mg/mL PAH solution in water was injected into the capillary with 0.01 mL/min for 20 minutes, and then Mill-Q water was continuously flowing to thorough rinsing the PAH-modified capillary so that the unbound and/or weakly absorbed PAH molecules were completely removed from the multi holes.

Synthesis of Gold Nanoparticles

Gold nanoparticles were synthesized using UV-assisted Photo-chemical method as described in the previous report.[35] Briefly, to achieve gold nanoparticles which have an average size of 117 nm in diameter, a molar ratio of 1:1.7 for HAuCl$_4$ and sodium citrate were stirred for ~2 minutes and then placed under a UV lamp (Dymax 2000-EC UV curing light source flood lamp system). The sample was then under continuous stirring for 10 minutes until the color of the solution changed from yellow to reddish or orange.

Raman System for SERS Measurement

Raman and SERS measurement were carried out with the custom made Raman spectroscopy system, consisting of a 785 nm excitation laser (Process instruments PI-ECL-785-300-FC-SH) and a spectrometer (Horiba Scientific iHR550, focal length 550 mm) equipped with a 600 grooves per mm grating and a spectroscopy grade CCD. An aspheric lens (NA=0.55 and f=4.51 mm) was used for delivery of the laser excitation and collection of the Raman signal. The excitation light was focused onto a spot of approximately 3 µm in diameter. All the Raman data was acquired with 6 mW excitation power and 2 seconds exposure time.

Figure 7:
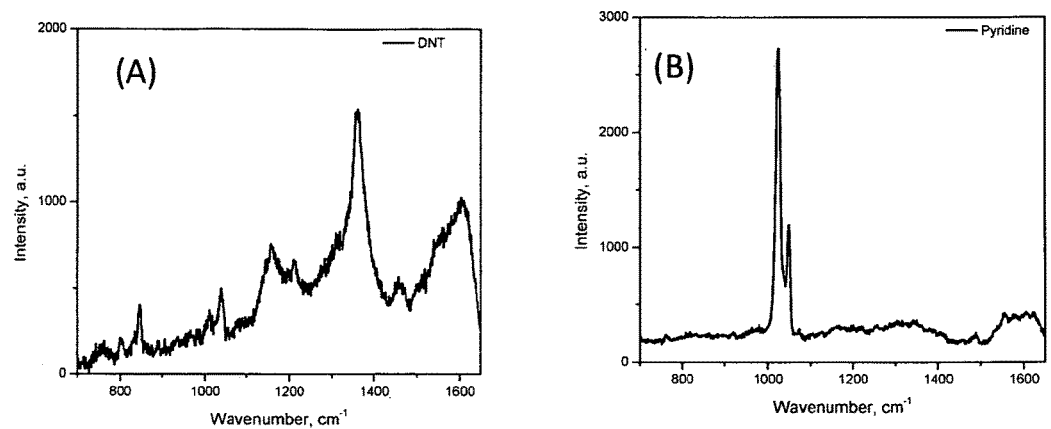
FIG. 7 is an example of surface enhanced Raman scattering (SERS) detection of vapors using the multi-hole capillary coated with gold nanoparticles FIG. 8 demonstrates excitation at transverse direction, and collection at longitudinal direction

An example of surface enhanced Raman scattering (SERS) detection of vapors using the multi-hole capillary coated with gold nanoparticles is shown in FIG. 7. FIG. 7(A) shows the DNT signature peaks: 834 cm$^{-1}$ —NO2 out-of-plane bending modes, 1009 cm$^{-1}$-aromatic ring breathing mode 1327 cm$^{-1}$ —NO2 stretching modes. FIG. 7(B) shows the pyridine signature peaks: Strong peak at ~1000 cm$^{-1}$ —C═C and C═N stretching modes.

Further non-limiting descriptions of various embodiments is provided in the Figures.

FIG. 7 is an example of surface enhanced Raman scattering (SERS) detection of vapors using the multi-hole capillary coated with gold nanoparticles.

In order to fully take advantage of the multi-hole capillary for fluorescence detection, we designed several system configurations but not limited to those as follows.

Figure 8:
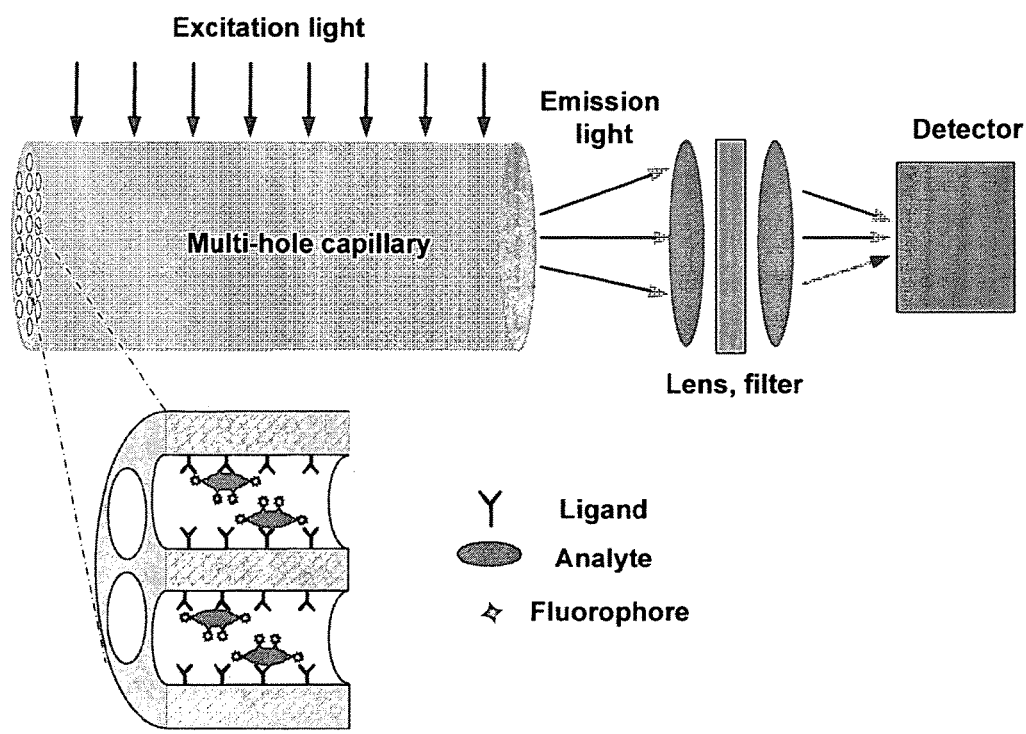

FIG. 8 illustrates fluorescence detection by excitation at transverse direction, and collection at longitudinal direction.

Figure 9:
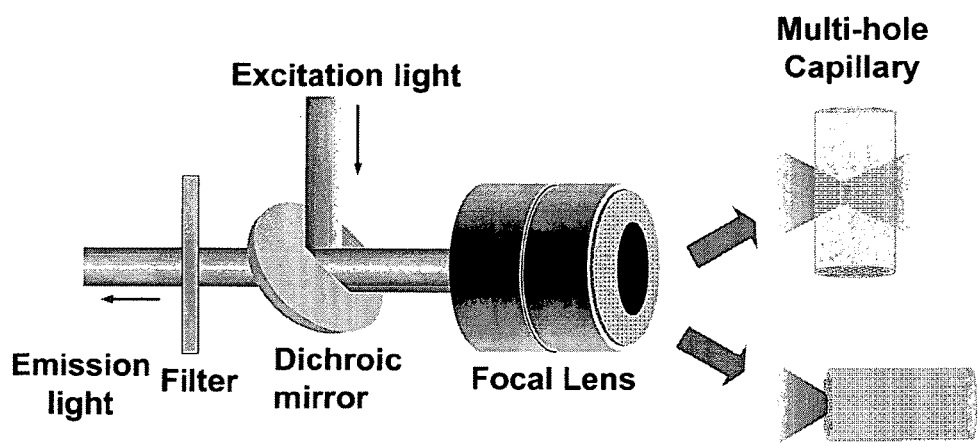
FIG. 9 illustrates integration of excitation and collection at transverse (top) or longitudinal (bottom) direction

FIG. 9 illustrates integration of excitation and collection at transverse (top) or longitudinal (bottom) direction.

Figure 10:
FIG. 10 is a perspective view of an analysis plate with a plurality of through holes having multi-hole capillaries in the through holes for high-throughput fluorescence detection. It is designed to be compatible with commercial fluorescence or luminescence readers.

FIG. 10 is a drawing of an analysis plate used for high-throughput fluorescence detection (which can be designed to be compatible with commercial fluorescence readers).

Figure 11:
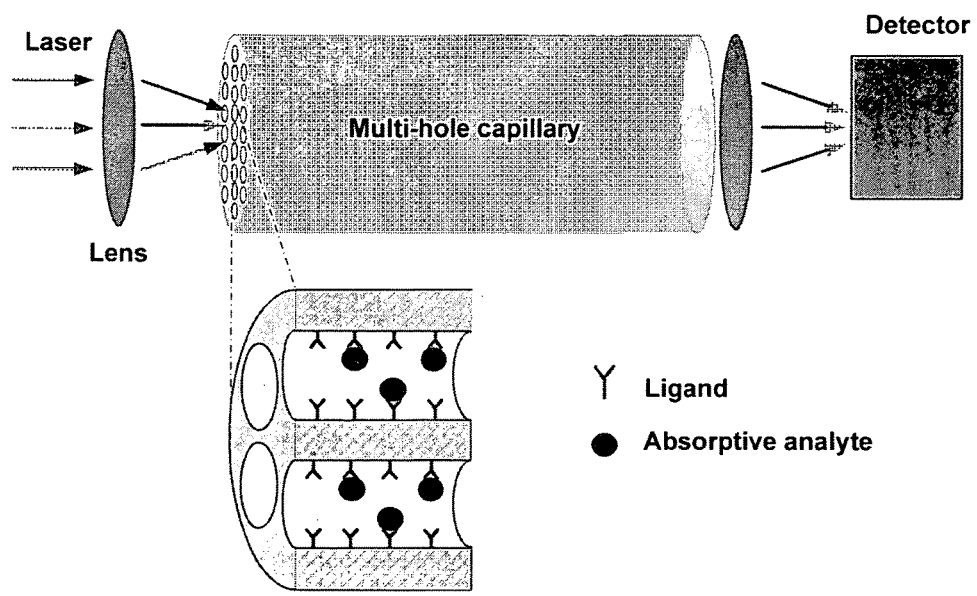
FIG. 11 illustrates a configuration for absorption detection in the longitudinal direction.

FIG. 11 illustrates absorption detection taking advantage of the light guiding properties in all channels of the multi-hole capillary. The absorptive analyte can be in liquid or vapor phase.

Laser Detection Volume

Figure 12:
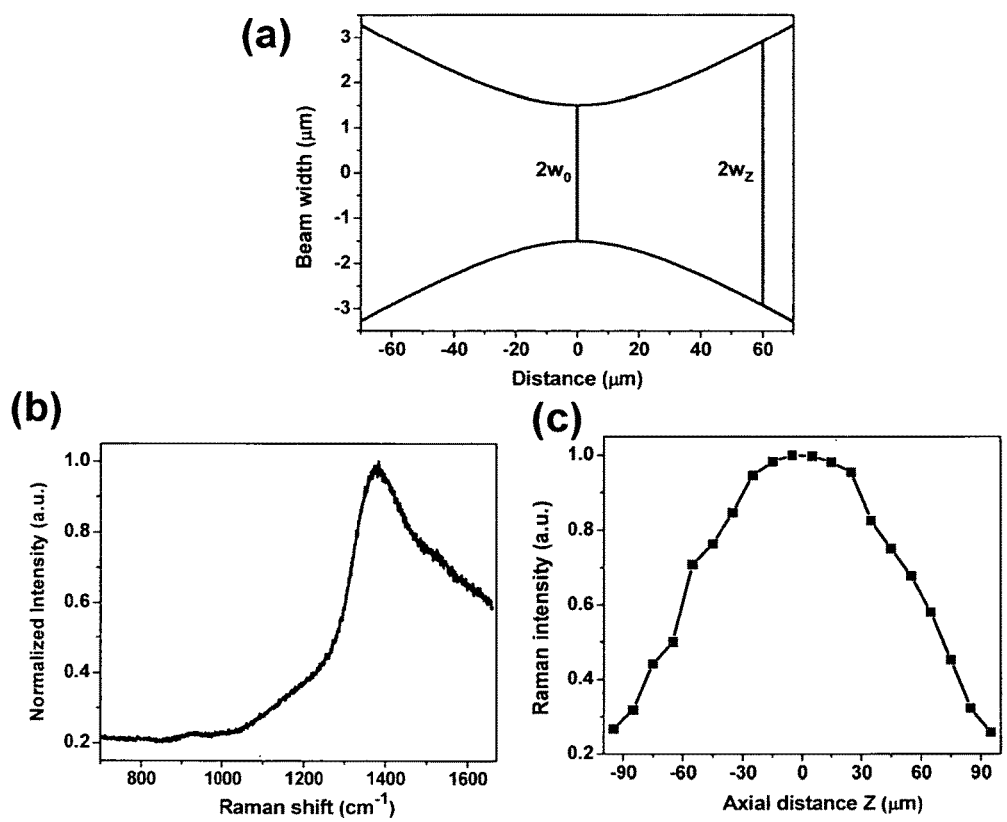
FIG. 12 (a) The Gaussian laser beam width along the propagation direction, and $2w_0=3$ μm at $Z=0$, $2w_z=5.8$ μm at $Z=60$ μm. (b) The typical normal Raman spectrum of a glass slide. (c) The Raman intensity at 1380 cm$^{-1}$ of the glass slide varies with the relative distance between the laser probe beam and the glass slide.

In our Raman measurements, the laser detection volume is determined by both the excitation laser and Raman signal collection optics. A 785 nm excitation laser was used, and the excitation light was focused onto a spot of approximately 3 µm in diameter. Its Gaussian beam width along the propagation direction varies with the distance from the focal point, as shown in FIG. 12 (a).

In order to determine the effective light penetration length, we performed a control experiment using a 180-µm-thick glass slide as a reference sample. The glass slide was put perpendicularly to the light propagation direction, and its normal Raman spectrum was measured and shown in FIG. 12(b), which had a characteristic Raman shift at 1380 cm$^{-1}$. To test the response of the Raman system to the 180-µm thick glass slide, we adjusted the relative distance between the glass slide and the laser probe beam, and measured the change of the Raman intensity of glass at 1380 cm$^{-1}$, shown in FIG. 12 (c). Using the convolution theory, we estimated the effective light penetration length was about 120 µm. Thus, the total detection volume was approximately $1.6 \times 10^3$ µm$^3$ for the multi-hole capillary used in our SERS experiments.

Extinction Spectrum of Gold Nanoparticles

FIG. 13 shows the extinction spectrum of the gold nanoparticles in solution with a concentration of $4 \times 10^{12}$ particles/mL. The gold nanoparticles have the maximal extinction at 570 nm, twice as high as at 785 nm (our excitation laser wavelength used in the experiments).

Enhancement of the Multi-Hole Capillary

Figure 14:
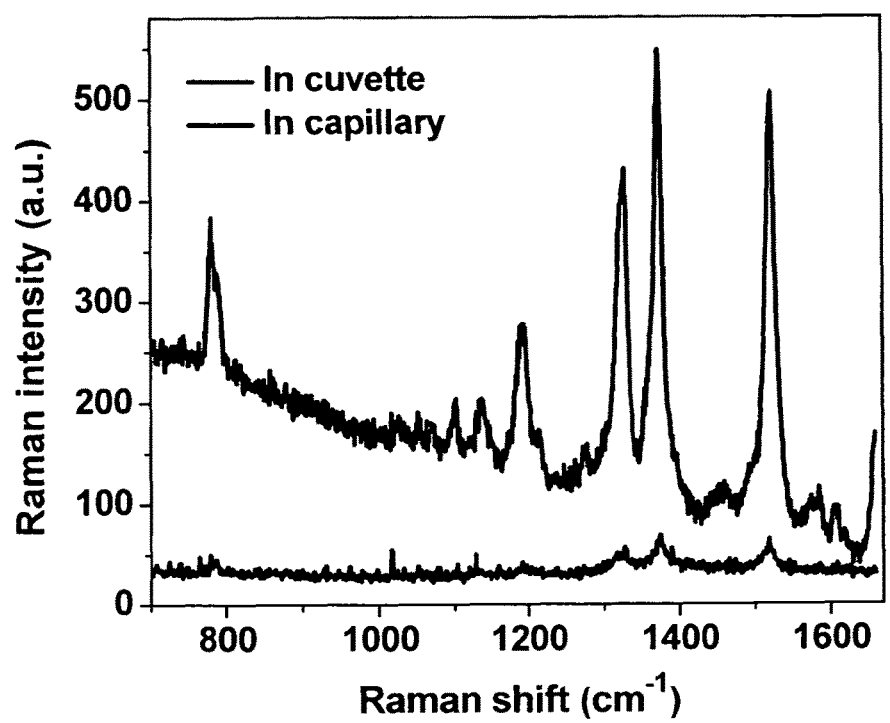
FIG. 14 shows the normal Raman spectra of $1\times10^{-2}$ M R6G in a 1-mL glass cuvette and in the multi-hole capillary, respectively.

To investigate the enhancement contribution from the multi-hole capillary, we performed a control experiment, where the normal Raman spectra of $1 \times 10^{-2}$ M R6G loaded in a 1-mL glass cuvette and in the multi-hole capillary were measured, respectively. The results in FIG. 14 show that over 20 fold enhancement was achieved using the multi-hole capillary by comparing the Raman intensity of characteristic R6G band at 1369 cm$^{-1}$.

Measurement of Transmission Loss

Figure 15:
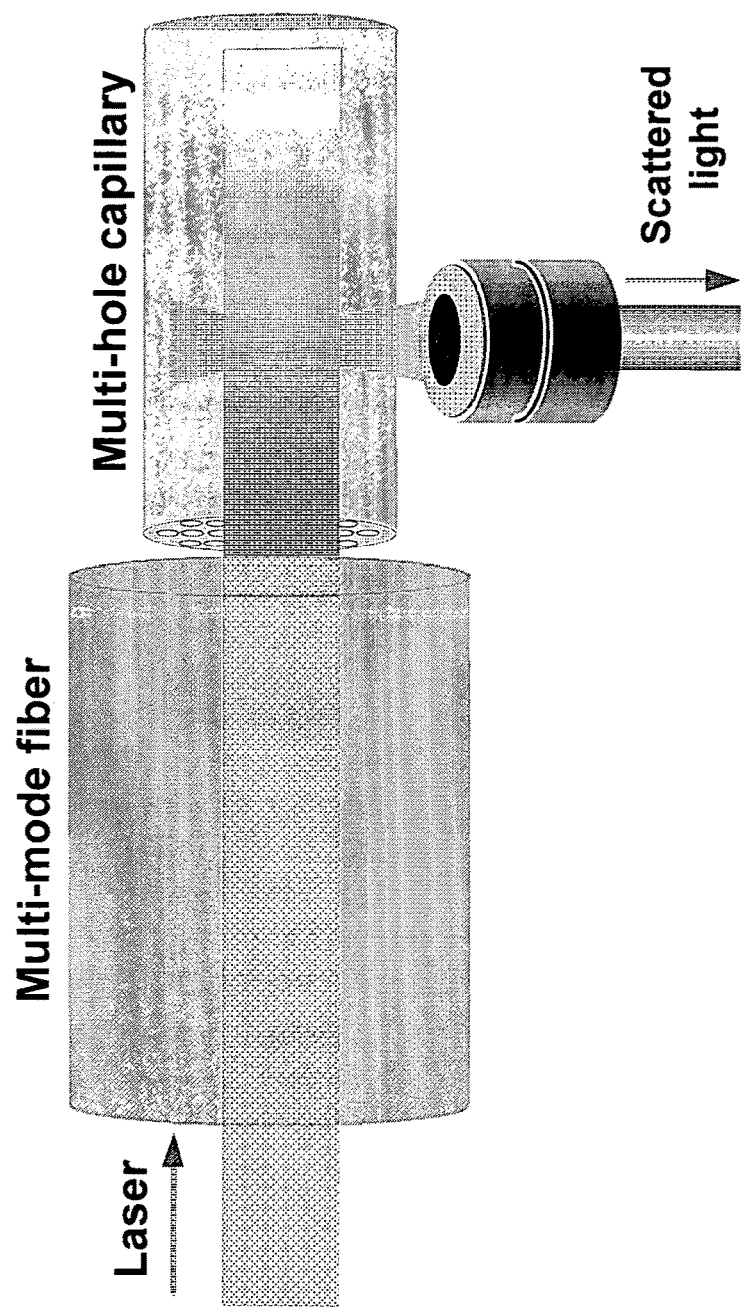
FIG. 15 shows a schematic of experimental setup measuring the transmission loss of a multi-hole capillary immobilized with gold nanoparticles.

In order to obtain the transmission loss of a short-length capillary (~3 mm) immobilized with gold nanoparticles, we adopted the experimental configuration as shown in FIG. 15. The laser light from the excitation source (785 nm diode laser) was transmitted via a multi-mode fiber with a core diameter of 50 µm (AFS50/125Y, Thorlabs, Inc.) into the multi-hole capillary in the longitudinal direction, and it was absorbed and scattered by the gold nanoparticles immobilized in the capillary. The scattered light at a certain position was collected using an objective lens into a spectrometer. By comparing the intensity of the scattered light at a series of positions along the light propagation direction, we are able to calculate the transmission loss within the multi-hole capillary, as shown in FIG. 5(b).

Fabrication and Use of an Analysis Plate

Figure 16:
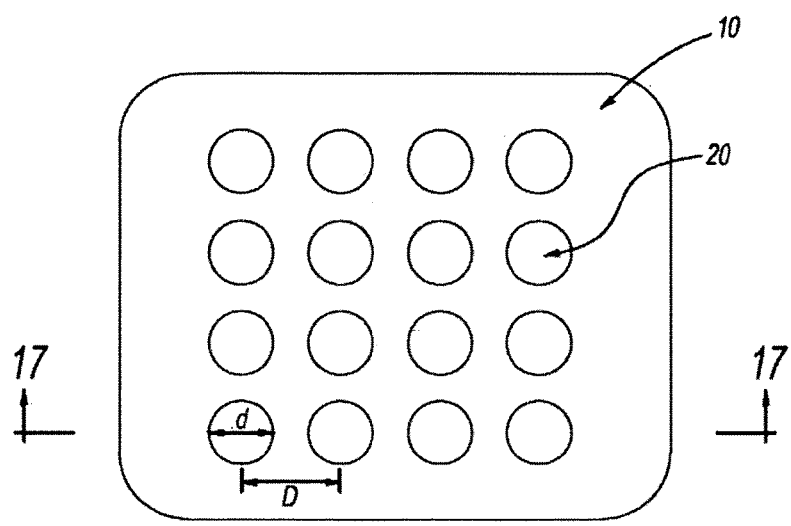
FIG. 16 is a plan view of an analysis plate.
Figure 17:
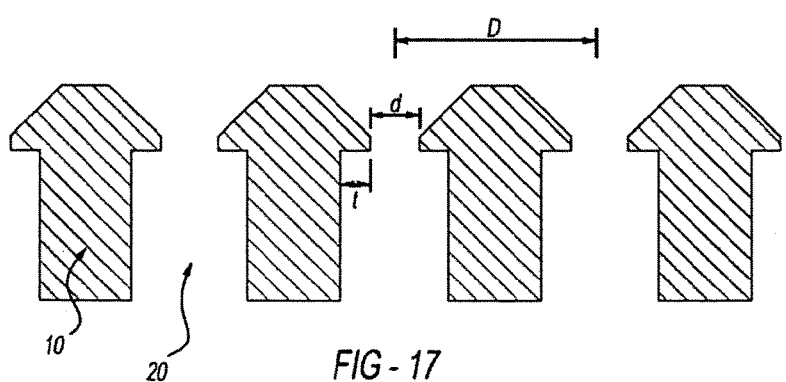
FIG. 17 is a cross sectional view of the plate of FIG. 16.
Figure 18:
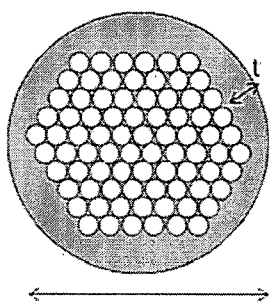
FIG. 18 illustrates a multi-hole capillary
Figure 19:
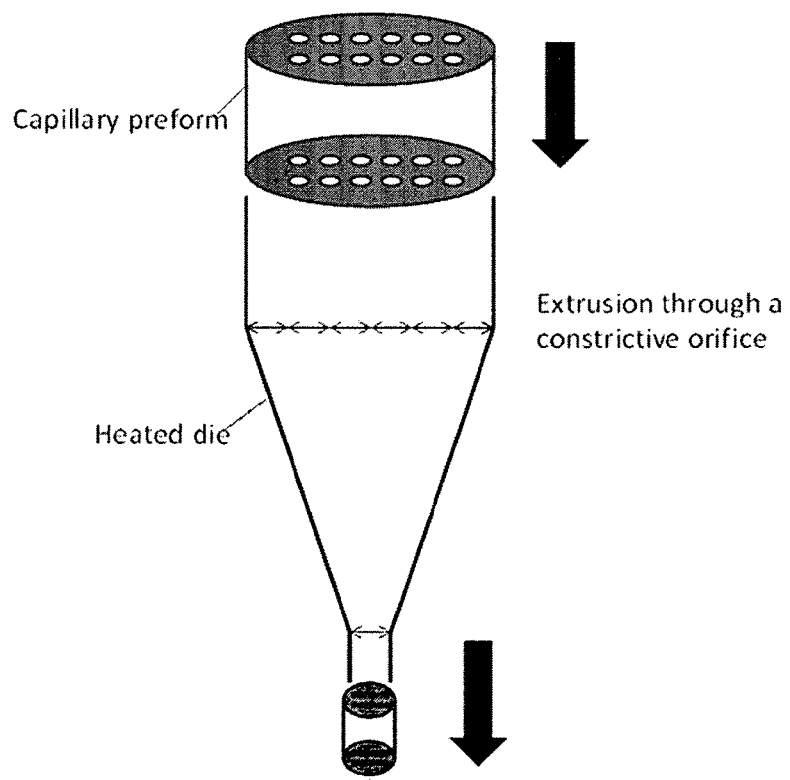
FIG. 19 illustrates an example of how to fabricate a multi-hole capillary.
Figure 20:
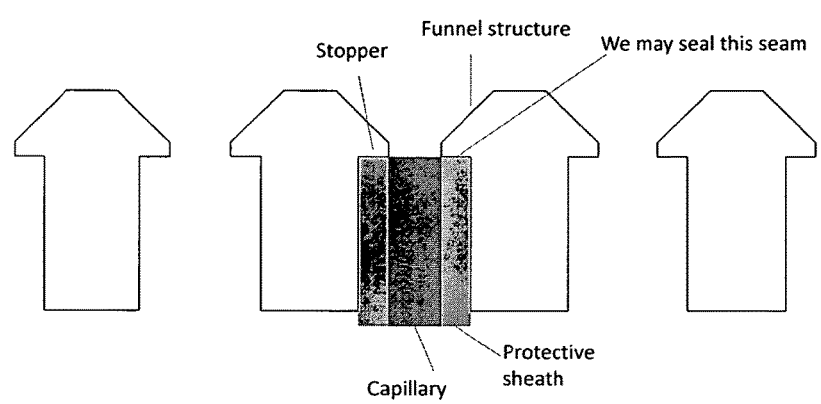
FIG. 20 shows a cross-sectional view of a 96-well plate after the capillary is inserted.

FIGS. 16 and 17 illustrate an embodiment of an analysis plate. The plate of FIG. 16 has a base or solid substrate 10 in which there are a number of through-holes 20 between and connecting first and second major surfaces of the plate. As shown, the through-holes are spaced apart by a repeat distance D. Each well has a diameter d. As shown in FIG. 17 in cross section, the individual wells 20 are spaced apart by a distance D and are characterized by an opening diameter d. In embodiments like the one shown in FIG. 17, each well has an overhang t which, as shown in FIG. 20, can accommodate a protective sheath or stopper around the multi-hole capillary In a preferred embodiment, the analysis plate has at least 96 through-holes, which serve as "wells" for analysis. Another embodiment provides a 384 well plate. The number of wells in a plate is limited only by the machining process used to make the plate and the capabilities of the high throughput reader utilized in the method. In an exemplary embodiment, a plastic plate is made using molding and drilling (FIG. 16). Next, a capillary bundle is fabricated with a sheath outside. This can be done by making a capillary bundle first and then inserting it inside a sheath, or by drawing or extruding microstructured polymer or glass fibers from a preform (FIGS. 18 and 19).

Figure 21:
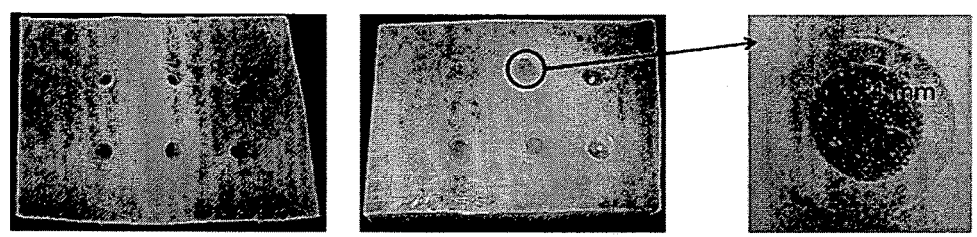
FIG. 21 is a photograph of a na analysis plate showing an inserted multi-hole capillary.

Then, the capillary is cut to a desired length and is inserted into the plate, for example a 96 well plate (see FIGS. 20 and 21).

Figure 22:
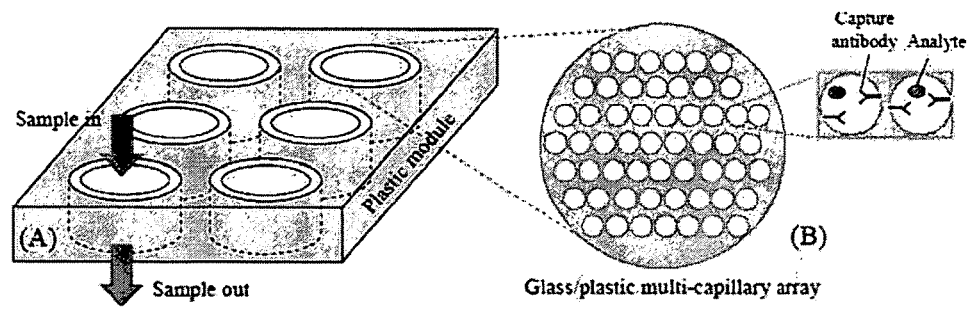
FIG. 22 illustrates the structure of an analysis plate.
Figure 23:
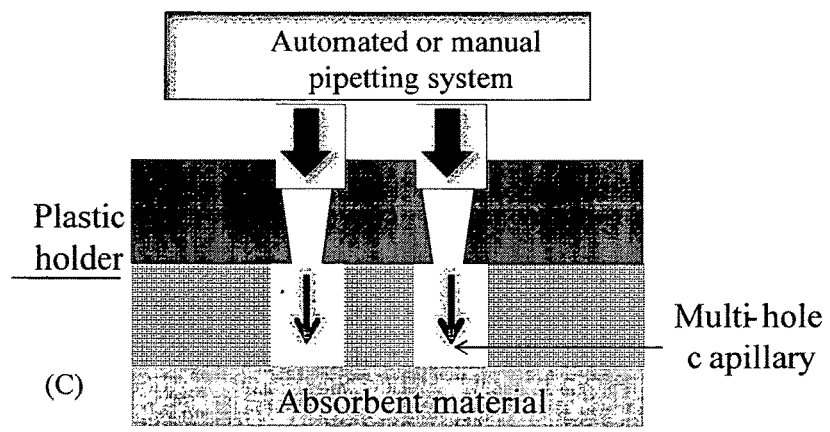
FIG. 23 illustrates a method of filling the analysis plate with analyte.
Figure 24:
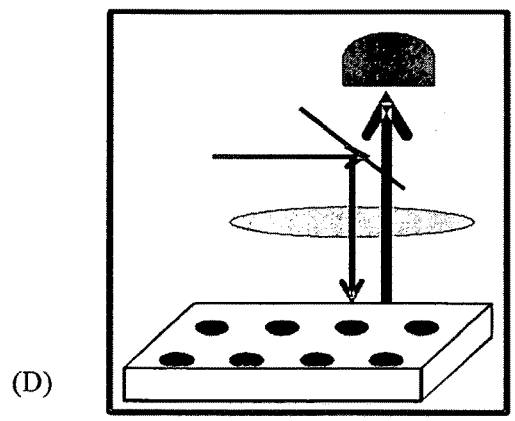
FIG. 24 illustrates one configuration for detecting fluorescence, luminescence, or absorption from the analysis plate.

The experimental setup is further illustrated in FIGS. 22-24. Sample and buffer are added from the top of the plate and wicked through the capillary by an absorbent pad placed under the plate. Detection can be carried from the top of the plate, as illustrated in FIG. 24 showing the incident beam and mirror (thinner arrows), absorption signal (or fluorescence or luminescence) represented with the thicker arrow, optics, and detector.

Figure 25:
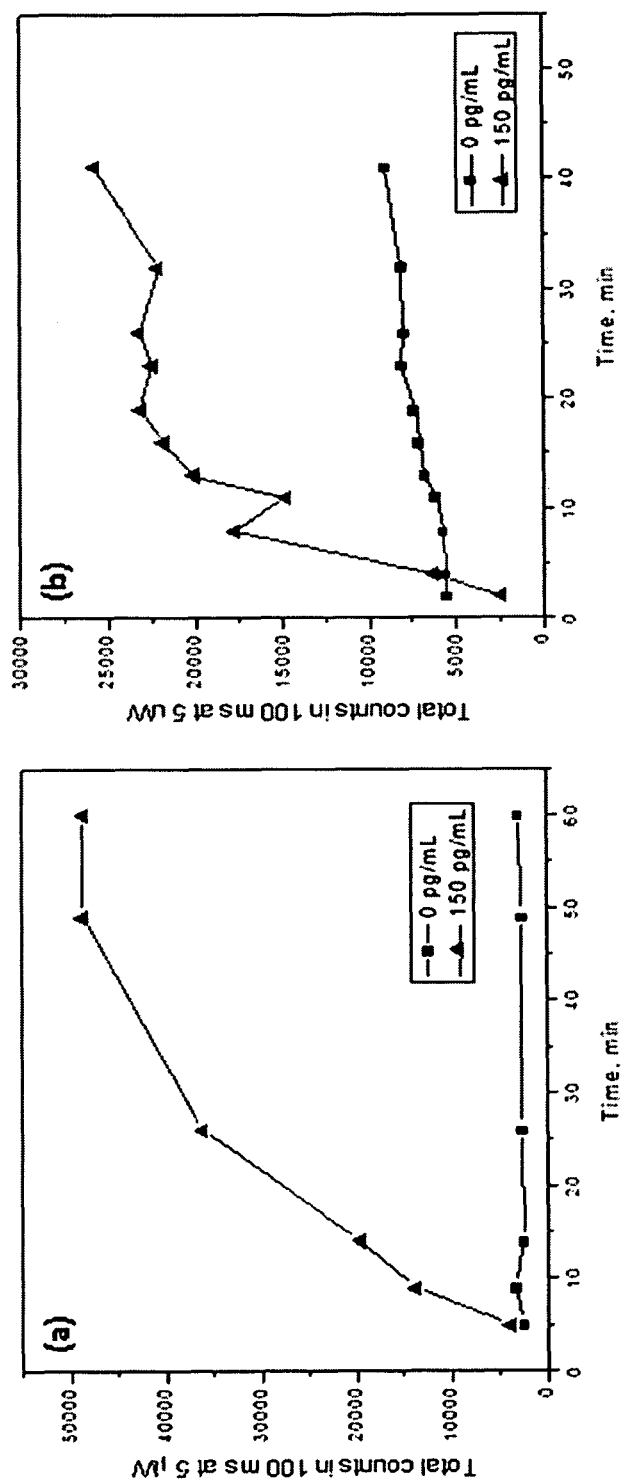
FIG. 25 shows a comparison of adsorption kinetics. (a) Regular 96 well plate. (b) Multi-hole polystyrene capillary with each hole's inner diameter of 125 μm.

FIG. 25 exhibits the comparison of adsorption kinetic of commercially available optimizer 96 well plate with currently developed polystyrene capillary bundle. In this experiment, concentration of 150 pg/mL and 0 pg/mL (blank sample) of human interleukin 6 (IL-6) were used as standard and control samples respectively. In the case of regular well plate (FIG. 25a), about 50 min is required to reach the plateau (the highest adsorption point of analyte), but only 10 min is required to reach that point in polystyrene multi-hole capillary (FIG. 25b), which results in fast analyte capturing ability and shorter assay time.

Figure 26:
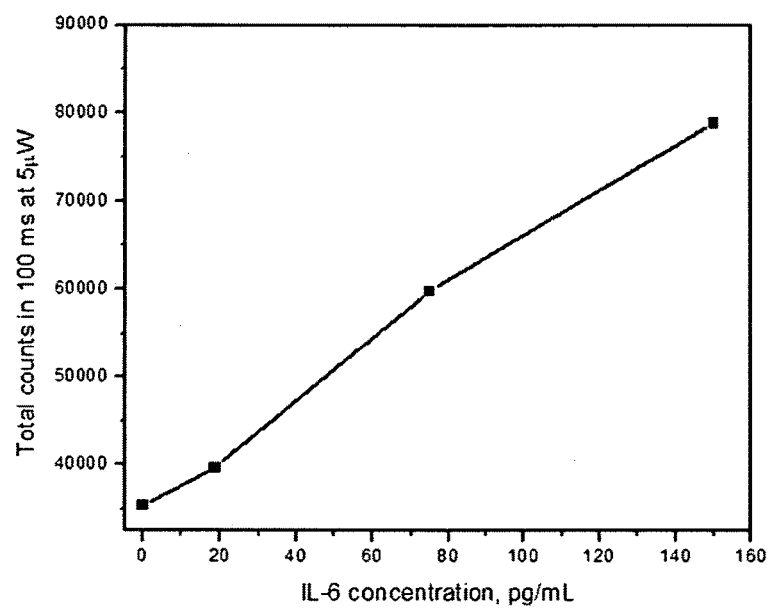
FIG. 26 shows a standard curve for IL-6 detection using multi-hole μm polystyrene capillary with 125 μm inner diameter for each hole.

We also observed a linear range of concentration dependent curve between 18.75 and 150 pg/mL (FIG. 26).

For some applications 96-well plates are not needed, and the multi-hole capillary can be inserted instead into a pipette tip or a needle that can be used with a pipette or a syringe. In this case, the above funnel structure in FIGS. 17 and 20 can be designed to be compatible with pipette or syringe.

In summary, we have developed a novel optofluidic SERS-active platform using a flow-through multi-hole capillary, which provides a unique 3-D configuration for large SERS-active area, inherent flow channels for sample delivery, and well-defined structure for light guiding. It also allows for simple, costly-efficient fabrication, and low sample consumption. Moreover, ultrasensitive SERS detection with an enhancement factor of over $10^{10}$ and a detection limit better than 100 fM for R6G molecules, has been achieved. Adjustments of experimental conditions, including the use of excited laser source close to the resonances of analyte molecules and metallic nanoparticles,[39] optimization of metallic nanoparticle density and the accumulation length,[23] and the use of modifications of the nanoparticle surfaces to enhance selected interactions between analyte molecules and the sensor,[40] are expected to yield further improvements in sensitivity and selectivity using the SERS-active multi-hole capillary. In addition, the optofluidic platform provides facile integration of the sensing elements into a range of capillary and microfluidic devices for bio/chemical detection. For example, integrating with the label-free biosensor demonstrated recently[30] can provide complementary information on molecular interaction.[41,42] We believe that the robust flow-through optofluidic SERS platform described here will drastically enhance the applicability of SERS-based chemical and biomolecular detection.

REFERENCES

1 Fleischmann, M., Hendra, P. J. & McQuillan, A. J. Raman spectra of pyridine adsorbed at a silver electrode. *Chem. Phys. Lett.* 1974, 26, 163-166.
2 Jeanmaire, D. L. & Van Duyne, R. P. Surface raman spectroelectrochemistry: Part I. Heterocyclic, aromatic, and aliphatic amines adsorbed on the anodized silver electrode. *J. Electroanal. Chem. Interfacial Electrochem.* 1977, 84, 1-20.
3 Kneipp, K. et al. Single molecule detection using surface-enhanced Raman scattering (SERS). *Phys. Rev. Lett.* 1997, 78, 1667.
4 Nie, S. & Emory, S. R. Probing single molecules and single nanoparticles by surface-enhanced Raman scattering. *Science* 1997, 275, 1102-1106.
5 Baker, G. A. & Moore, D. S. Progress in plasmonic engineering of surface-enhanced Raman-scattering substrates toward ultra-trace analysis. *Anal. Bioanal. Chem.* 2005, 382, 1751-1770.
6 Dieringer, J. A. et al. Surface-enhanced Raman excitation spectroscopy of a single Rhodamine 6G molecule. *J. Am. Chem. Soc.* 2008, 131, 849-854.
7 Charles, J. C., Zhida, X., Hsin-Yu, W., Gang, L. L. & Brian, T. C. Surface-enhanced Raman nanodomes. *Nanotechnology* 2010, 21, 415301.
8 Li, W. D., Ding, F., Hu, J. & Chou, S. Y. Three-dimensional cavity nanoantenna coupled plasmonic nanodots for ultrahigh and uniform surface-enhanced Raman scattering over large area. *Opt. Express* 2011, 19, 3925-3936.
9 Caldwell, J. D. et al. Plasmonic nanopillar arrays for large-area, high-enhancement surface-enhanced Raman scattering sensors. *ACS Nano* 2011, 5, 4046-4055.
10 Chan, S., Kwon, S., Koo, T. W., Lee, L. P. & Berlin, A. A. Surface-enhanced Raman scattering of small molecules from silver-coated silicon nanopores. *Adv. Mater.* 2003, 15, 1595-1598.
11 Jiao, Y. et al. Patterned nanoporous gold as an effective SERS template. *Nanotechnology* 2011, 22.
12 Zhang, L., Lang, X., Hirata, A. & Chen, M. Wrinkled nanoporous gold films with ultrahigh surface-enhanced Raman scattering enhancement. *ACS Nano* 2011, 5, 4407-4413.
13 Psaltis, D., Quake, S. R. & Yang, C. Developing optofluidic technology through the fusion of microfluidics and optics. *Nature* 2006, 442, 381-386.
14 Monat, C., Domachuk, P. & Eggleton, B. J. Integrated optofluidics: A new river of light. *Nat. Photon.* 2007, 1, 106-114.
15 Erickson, D., Sinton, D. & Psaltis, D. Optofluidics for energy applications. *Nat Photon* 2011, 5, 583-590.
16 Schmidt, H. & Hawkins, A. R. The photonic integration of non-solid media using optofluidics. *Nat Photon* 2011, 5, 598-604.
17 Fan, X. & White, I. M. Optofluidic microsystems for chemical and biological analysis. *Nat Photon* 2011, 5, 591-597.
18 Yin, Y., Qiu, T., Zhang, W. J. & Chu, P. K. Recent developments in optofluidic-surface-enhanced Raman scattering systems: Design, assembly, and advantages. *J. Mater. Res.* 2011, 26, 170-185.
19 Amezcua-Correa, A. et al. Surface-enhanced Raman scattering using microstructured optical fiber substrates. *Adv. Funct. Mater.* 2007, 17, 2024-2030.
20 Cox, F. M., Argyros, A., Large, M. C. J. & Kalluri, S. Surface enhanced Raman scattering in a hollow core microstructured optical fiber. *Opt. Express* 2007, 15, 13675-13681.
21 Yang, X. et al. High-sensitivity molecular sensing using hollow-core photonic crystal fiber and surface-enhanced Raman scattering. *J. Opt. Soc. Am. A* 2010, 27, 977-984.
22 Khaing Oo, M. K., Han, Y., Kanka, J., Sukhishvili, S. & Du, H. Structure fits the purpose: photonic crystal fibers for evanescent-field surface-enhanced Raman spectroscopy. *Opt. Lett.* 2010, 35, 466-468.
23 Han, Y. et al. Towards full-length accumulative surface-enhanced Raman scattering-active photonic crystal fibers. *Adv. Mater.* 2010, 22, 2647-2651.
24 Measor, P. et al. On-chip surface-enhanced Raman scattering detection using integrated liquid-core waveguides. *Appl. Phys. Lett.* 2007, 90, 211107.
25 Ko, H. & Tsukruk, V. V. Nanoparticle-Decorated Nanocanals for Surface-Enhanced Raman Scattering. *Small* 2008, 4, 1980-1984.
26 Ko, H., Chang, S. & Tsukruk, V. V. Porous Substrates for Label-Free Molecular Level Detection of Nonresonant Organic Molecules. *ACS Nano* 2009, 3, 181-188.
27 Choi, I., Huh, Y. S. & Erickson, D. Size-selective concentration and label-free characterization of protein aggregates using a Raman active nanofluidic device. *Lab Chip* 2011, 11, 632-638.
28 Wang, M., Jing, N., Chou, I. H., Cote, G. L. & Kameoka, J. An optofluidic device for surface enhanced Raman spectroscopy. *Lab Chip* 2007, 7, 630-632.
29 Liu, J., White, I. & DeVoe, D. L. Nanoparticle-functionalized porous polymer monolith detection elements for surface-enhanced Raman scattering. *Anal. Chem.* 2011, 83, 2119-2124.
30 Guo, Y. et al. Optofluidic Fabry-Perot cavity biosensor with integrated flow-through micro-/nanochannels. *Appl. Phys. Lett.* 2011, 98, 041104.
31 Escobedo, C., Brolo, A. G., Gordon, R. & Sinton, D. Flow-through vs flow-over: analysis of transport and binding in nanohole array plasmonic biosensors. *Anal. Chem.* 2010, 82, 10015-10020.
32 van Eijkelenborg, M. Imaging with microstructured polymer fibre. *Opt. Express* 2004, 12, 342-346.
33 Apetrei, A. M. et al. A dense array of small coupled waveguides in fiber technology: trefoil channels of microstructured optical fibers. *Opt. Express* 2008, 16, 20648-20655.
34 Peacock, A. C., Amezcua-Correa, A., Yang, J., Sazio, P. J. & Howdle, S. M. Highly efficient surface enhanced Raman scattering using microstructured optical fibers with enhanced plasmonic interactions. *Appl. Phys. Lett.* 2008, 92, 141113.
35 Khaing Oo, M. K., Chang, C. F., Sun, Y. & Fan, X. Rapid, sensitive DNT vapor detection with UV-assisted photo- 36 Hildebrandt, P. & Stockburger, M. Surface-enhanced resonance Raman spectroscopy of Rhodamine 6G adsorbed on colloidal silver. *J. Phys. Chem.* 1984, 88, 5935-5944.
37 Piorek, B. D. et al. Free-surface microfluidic control of surface-enhanced Raman spectroscopy for the optimized detection of airborne molecules. *Proc. Natl. Acad. Sci. USA* 2007, 104, 18898-18901.
38 Yu, H.-Z., Zhang, J., Zhang, H.-L. & Liu, Z.-F. Surface-enhanced Raman scattering (SERS) from azobenzene self-assembled "sandwiches". *Langmuir* 1998, 15, 16-19.
39 Lim, D. K. et al. Highly uniform and reproducible surface-enhanced Raman scattering from DNA-tailorable nanoparticles with 1-nm interior gap. *Nat. Nanotechnol.* 2011, 6, 452-460.
40 Galarreta, B. C., Norton, P. R. & Lagugné-Labarthet, F. o. SERS detection of streptavidin/biotin monolayer assemblies. *Langmuir* 2011, 27, 1494-1498.
41 Jiao, Y., Koktysh, D. S., Phambu, N. & Weiss, S. M. Dual-mode sensing platform based on colloidal gold functionalized porous silicon. *Appl. Phys. Lett.* 2010, 97, 153125.
42 Meyer, S. A., Le Ru, E. C. & Etchegoin, P. G. Combining surface plasmon resonance (SPR) spectroscopy with surface-enhanced Raman scattering (SERS). *Anal. Chem.* 2011, 83, 2337-2344.

We claim:

1. A method of detecting an analyte bound to a surface by use of absorption, luminescence, or fluorescence spectroscopy comprising exciting the analyte with electromagnetic radiation and detecting the absorption, luminescence, or fluorescence, wherein the surface onto which the analyte is bound is the interior surface of a micro-/nanofluidic channel in a multi-hole capillary, wherein the multi-hole capillary provides a plurality of micro-/nanofluidic channels for flow-through analyte delivery, wherein the micro-/nanofluidic channels are characterized by a dimension of 100 nm-200 microns, and wherein the multi-hole capillary does not have a photonic crystal structure.

2. The method of claim 1, wherein the multi-hole capillary is made of fused silica glass or borosilicate glass.

3. The method of claim 1, comprising exciting in the transverse configuration and detecting in the transverse configuration.

4. The method of claim 1, comprising exciting in the transverse configuration and detecting in the longitudinal configuration.

5. The method of claim 1, comprising exciting in the longitudinal configuration and detecting in the transverse configuration.

6. The method of claim 1, comprising exciting in the longitudinal configuration and detecting in the longitudinal configuration.

7. The method of claim 1, wherein the dimension is 1-5 microns.

8. The method of claim 1, wherein the analyte is bound to the surface as part of an antibody complex.

9. A method of detecting an analyte by use of absorption, luminescence, or fluorescence spectroscopy comprising exciting the analyte with electromagnetic radiation or causing the analyte to luminescence, and detecting the luminescence, absorption, or fluorescence, wherein the analyte is a substrate of an enzyme attached to an antibody attached to the interior surface of a micro-/nanofluidic channel in a multi-hole capillary, wherein the multi-hole capillary provides a plurality of micro-/nanofluidic channels for flow-through analyte delivery, wherein the micro-/nanofluidic channels are characterized by a dimension of 10 nm-200 microns, and wherein the multi-hole capillary does not have a photonic crystal structure.

10. The method of claim 1, wherein the multi-hole capillary is made of glass and contains 10-300,000 micro-/nanofluidic channels.

11. The method of claim 1, wherein the multi-hole capillary is made of glass and contains 200-300,000 micro-/nanofluidic channels.

12. The method of claim 1, wherein the multi-hole capillary is made of glass and contains 1000-300,000 micro-/nanofluidic channels.

13. The method of claim 1, wherein the multi-hole capillary is made of glass and contains 1000-20,000 micro-/nanofluidic channels.

14. The method of claim 1, wherein the multi-hole capillary is made of glass and contains 1000-10,000 micro-/nanofluidic channels.

15. The method of claim 1, wherein the dimension of the channels is 100 nm-20 microns.

* * * * *